(12) United States Patent
Windisch et al.

(10) Patent No.: US 6,730,156 B1
(45) Date of Patent: May 4, 2004

(54) CLUSTERED PARTICLE DENTAL FILLERS

(75) Inventors: Mark Steven Windisch, Stillwater, MN (US); Xiaodong Zhang, Woodbury, MN (US); Richard Paul Rusin, Woodbury, MN (US); Sumita Basu Mitra, West St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/428,830

(22) Filed: Oct. 28, 1999

(51) Int. Cl.$^7$ ................................................. C09B 1/28
(52) U.S. Cl. .................. 106/35; 523/113; 523/114; 523/115; 523/116; 523/117; 106/401; 106/425; 106/426; 106/428; 106/461; 106/479; 106/481; 106/436; 106/442; 106/450; 106/454; 106/456; 106/459
(58) Field of Search ................ 106/35, 425, 426, 106/428, 461, 479, 481, 482, 401, 436, 442, 450, 454, 456, 459; 523/113, 114, 115, 116, 118; 524/434, 430, 432, 433, 436, 413, 408, 403, 406, 407, 492, 493, 497, 780, 781, 783, 784, 785, 789

(56) References Cited

U.S. PATENT DOCUMENTS

| | | |
|---|---|---|
| 2,984,628 A | 5/1961 | Alexander et al. |
| 3,018,262 A | 1/1962 | Schroeder |
| 3,066,112 A | 11/1962 | Bowen |
| 3,117,099 A | 1/1964 | Proops et al. |
| 3,442,817 A | 5/1969 | Luebke |
| 3,514,252 A | 5/1970 | Levy, Jr. et al. |
| 3,539,533 A | 11/1970 | Lee et al. |
| 3,629,187 A | 12/1971 | Waller |
| 3,708,296 A | 1/1973 | Schlesinger |
| 3,709,706 A * | 1/1973 | Sowman ............. 501/103 |
| 3,709,866 A | 1/1973 | Waller |
| 3,729,313 A | 4/1973 | Smith |
| 3,741,769 A | 6/1973 | Smith |
| 3,751,399 A | 8/1973 | Lee et al. |
| 3,766,132 A | 10/1973 | Lee et al. |
| 3,808,006 A | 4/1974 | Smith |
| 3,860,556 A | 1/1975 | Taylor |
| 4,002,669 A | 1/1977 | Gross et al. |
| 4,069,055 A | 1/1978 | Crivello |
| 4,071,424 A | 1/1978 | Dart et al. |
| 4,115,346 A | 9/1978 | Gross et al. |
| 4,216,288 A | 8/1980 | Crivello |
| 4,250,053 A | 2/1981 | Smith |
| 4,250,311 A | 2/1981 | Crivello |
| 4,259,117 A | 3/1981 | Yamauchi et al. |
| 4,292,029 A | 9/1981 | Craig et al. |
| 4,308,190 A | 12/1981 | Walkowiak et al. |

(List continued on next page.)

FOREIGN PATENT DOCUMENTS

| | | |
|---|---|---|
| CA | 2202732 | 10/1997 |
| DE | 195 40 623 A1 | 5/1997 |
| EP | 94914 A2 | 11/1983 |
| EP | 0 173 567 | 3/1986 |
| EP | 0 184 467 A2 | 6/1986 |

(List continued on next page.)

OTHER PUBLICATIONS

Craig, "Restorative Dental Materials," 8th ed., 1989, p. 256.
Definition of "binary compound," Oct. 09, 1997, [retrieved on Feb. 16, 2001] Retrieved from the On–line Medical Dictionary using Internet <URL:http:/www.graylab.ac.uk/cgi–bin/omd?binary+compound>, 1 page.

(List continued on next page.)

*Primary Examiner*—C. Melissa Koslow

(57) ABSTRACT

A filler comprising a substantially amorphous cluster comprising non-heavy metal oxide particles and heavy metal oxide. The filler can be mixed into a hardenable resin to provide radiopaque dental materials having desirable strength and aesthetic character.

55 Claims, 1 Drawing Sheet

0.05 μm

U.S. PATENT DOCUMENTS

| | | | |
|---|---|---|---|
| 4,327,014 A | 4/1982 | Kawahara et al. | |
| 4,379,695 A | 4/1983 | Orlowski et al. | |
| 4,387,240 A | 6/1983 | Berg | |
| 4,389,497 A | 6/1983 | Schmitt et al. | |
| 4,394,403 A | 7/1983 | Smith | |
| 4,404,150 A | 9/1983 | Tsunekawa et al. | |
| 4,427,799 A | 1/1984 | Orlowski et al. | |
| 4,503,169 A | * 3/1985 | Randlev | 523/117 |
| 4,544,359 A | 10/1985 | Waknine | |
| 4,545,924 A | 10/1985 | Ritter, II | |
| 4,612,138 A | 9/1986 | Keiser | |
| 4,617,327 A | 10/1986 | Podszun | |
| 4,619,817 A | 10/1986 | Stambaugh et al. | |
| 4,642,126 A | 2/1987 | Zador et al. | |
| 4,649,165 A | 3/1987 | Kuhlmann | |
| 4,652,274 A | 3/1987 | Boettcher et al. | |
| 4,661,540 A | 4/1987 | Le et al. | |
| 4,696,955 A | 9/1987 | Kuhlmann | |
| 4,719,091 A | 1/1988 | Wusirika | |
| 4,737,593 A | 4/1988 | Ellrich et al. | |
| 4,746,685 A | 5/1988 | Masuhara et al. | |
| 4,769,351 A | 9/1988 | Soumiya et al. | |
| 4,772,511 A | 9/1988 | Wood et al. | |
| 4,772,530 A | 9/1988 | Gottschalk et al. | |
| 4,778,671 A | 10/1988 | Wusirika | |
| 4,784,794 A | 11/1988 | Kato | |
| 4,868,288 A | 9/1989 | Meier | |
| 4,874,450 A | 10/1989 | Gottschalk | |
| 4,886,624 A | 12/1989 | Gradeff et al. | |
| 4,923,905 A | 5/1990 | Masuhura et al. | |
| 4,927,560 A | 5/1990 | Osaka et al. | |
| 4,931,414 A | 6/1990 | Wood et al. | |
| 4,946,665 A | 8/1990 | Recasens et al. | |
| 4,954,414 A | 9/1990 | Adair et al. | |
| 4,985,229 A | 1/1991 | Obitsu et al. | |
| 4,985,340 A | 1/1991 | Palazzotto et al. | |
| 5,037,579 A | 8/1991 | Matchett | |
| 5,055,372 A | 10/1991 | Shanklin et al. | |
| 5,057,393 A | 10/1991 | Shanklin et al. | |
| 5,073,476 A | 12/1991 | Meier et al. | |
| 5,084,586 A | 1/1992 | Farooq | |
| 5,089,536 A | 2/1992 | Palazzotto | |
| 5,124,417 A | 6/1992 | Farooq | |
| 5,190,583 A | 3/1993 | Menzel et al. | |
| 5,234,870 A | 8/1993 | Osaka et al. | |
| 5,275,759 A | 1/1994 | Osaka et al. | |
| 5,332,429 A | 7/1994 | Mitra et al. | |
| 5,460,701 A | 10/1995 | Parker et al. | |
| 5,470,910 A | 11/1995 | Spanhel et al. | |
| 5,545,676 A | 8/1996 | Palazzotto et al. | |
| 5,558,849 A | 9/1996 | Sharp | |
| 5,593,781 A | 1/1997 | Nass et al. | |
| 5,609,675 A | * 3/1997 | Noritake et al. | 106/35 |
| 5,643,497 A | 7/1997 | Kaga et al. | |
| 5,648,407 A | 7/1997 | Goetz et al. | |
| 5,658,376 A | 8/1997 | Noguchi et al. | |
| 5,698,483 A | 12/1997 | Ong et al. | |
| 5,760,126 A | 6/1998 | Engle et al. | |
| 5,776,239 A | 7/1998 | Bruno | |
| 5,830,242 A | 11/1998 | Yao | |
| 5,856,373 A | 1/1999 | Kaisaki et al. | |
| 5,879,715 A | 3/1999 | Higgins et al. | |
| 5,886,069 A | * 3/1999 | Bolt | 523/223 |
| 5,935,275 A | 8/1999 | Burgard et al. | |
| 5,936,006 A | 8/1999 | Rheinberger et al. | |
| 5,942,559 A | 8/1999 | Voser et al. | 523/115 |
| 5,998,495 A | 12/1999 | Oxman et al. | |
| 6,025,406 A | 2/2000 | Oxman et al. | |
| 6,136,886 A | 10/2000 | Doguchi | |

FOREIGN PATENT DOCUMENTS

| | | |
|---|---|---|
| EP | 94914 B1 | 9/1986 |
| EP | 0 094 914 | 9/1986 |
| EP | 0 434 334 | 6/1991 |
| EP | 0 530 926 | 3/1993 |
| EP | 0 712 912 A2 | 5/1996 |
| EP | 0 841 304 A1 | 5/1998 |
| GB | 2310855 | 9/1997 |
| JP | 3-46407 | 6/1984 |
| JP | 4-72768 | 9/1985 |
| WO | WO 93/05875 | 4/1993 |
| WO | WO 96/34829 | 11/1996 |
| WO | WO 98/13008 | 4/1998 |
| WO | WO 99/17716 | 4/1999 |
| WO | WO 99/65453 | 12/1999 |
| WO | WO 00/03688 | 1/2000 |
| WO | WO00/20494 | 4/2000 |

OTHER PUBLICATIONS

Definition of "oxide," Oct. 09, 1997, [retrieved on Feb. 16, 2001]Retrieved from the On–line Medical Dictionary using Internet <URL:http://www.graylab.ac.uk/cgi–bin/omd?oxide>, 1 page.

*Grant and Hackh's Chemical Dictionary*, 5th Edition, Dr. Roger Grant, Ed., Title Page, Publication Page, p. 106 and p. 231 (1987).

W.B. Blumenthal, "The Chemical Behavior of Zirconium," D. Van Nostrand Company, Princeton, NJ, pp. 311–338.

"Routes to Deagglomerated Nanopowder by Chemical Synthesis," Burgard et al., *Mat. Res. Soc. Symp. Proc.*, vol. 346, 1994; pp. 101–107.

"Synthesis and Collodial Processing of Nanocrystalline (Y2O3–Stabilized) ZrO2 Powders by a Surface Free Energy Controlled Process," Burgard et al., *Mat. Res. Soc. Symp., Proc.*, vol. 432, 1997, pp. 113–121.

"The Role of Complexing Ligants in the Formation of Non–Aggregated Nanoparticles of Zirconia," Chatry et al., *Journal of Sol–Gel Science and Technology*, vol. 1, 1994, pp. 233–240.

"Determination of Polymerization Shrinkage Kinetics of Visible–Light–Cured Materials: Methods of Development," Dental Materials, Oct. 1991, pp. 281–286.

Japanese Patent Abstract for JP 1076919 A.
Japanese Patent Abstract for JP 1079015 A.
Japanese Patent Abstract for JP 1083518 A.
Japanese Patent Abstract for JP 1083519 A.
Japanese Patent Abstract for JP 1083520 A.
Japanese Patent Abstract for JP 1176225 A.
Japanese Patent Abstract for JP 2137729 A.
Japanese Patent Abstract for JP 2137730 A.
Japanese Patent Abstract for JP 2137731 A.
Japanese Patent Abstract for JP 2137732 A.
Japanese Patent Abstract for JP 3174326 A.
Japanese Patent Abstract for JP 4031307 A.
Japanese Patent Abstract for JP 4089319 A.
Japanese Patent Abstract for JP 7118016 A.
Japanese Patent Abstract for JP 8277114 A.
Japanese Patent Abstract for JP 9235119 A.
Japanese Patent Abstract for JP 58079818 A.
Japanese Patent Abstract for JP 58135131 A.
Japanese Patent Abstract for JP 59107969 A.
Japanese Patent Abstract for JP 60103033 A.
Japanese Patent Abstract for JP60137827 A.
Japanese Patent Abstract for JP 60176920 A.
Japanese Patent Abstract for JP 60255622 A.

Japanese Patent Abstract for JP 61227917 A.
Japanese Patent Abstract for JP 61270217 A.
Japanese Patent Abstract for JP 61141620 A.
Japanese Patent Abstract for JP 62065932 A.
Japanese Patent Abstract for JP 62091421 A.
Japanese Patent Abstract for JP 62128924 A.
Japanese Patent Abstract for JP 62212224 A.
Japanese Patent Abstract for JP 62226815 A.
Japanese Patent Abstract for JP 63002809 A.
Derwent Publications Ltd., Abstract for Japanese Pat. No. 54 077776 A, Jun. 21, 1979.
Cabot Corporation Product Brochure, "Cab–O–Sil® Untreated Fumed Silica Properties and Functions," Title page, Publication page, and pp. 3–5 (1978).
Degussa AG Product Brochure, Technical Bulletin Pigments, AEROSIL® as a Thickening Agent for Liquid Systems, No. 23, Title page, Publication page, and pp. 3 and 29 (Jul. 1989).
Degussa AG Product Brochure, "Technical Bulletin Pigments," AEROSIL® in Pharmaceuticals and Cosmetics, No. 49, Title page, Publication page, and pp. 5 and 6 (Sep. 1997).

55119USA6B—09/698,986 "Clustered Particle Dental Fillers" filed Oct. 27, 2000.

55200USA5A—09/428,374 "Zirconia Sol and Method of Making Same" filed Oct. 28, 1999.

54468USA1A—09/168,051, "Radiopaque Cationically Polymerizable Compositions Comprising a Radiopacifying Filler, and Method for Polymerizaing Same" filed Oct. 7, 1998.

C.W. Macosko, "Rheology Principles, Measurements, and Applications," VCH Publishers, Inc., New York, 1994, p. 92.

Surface 7 Colloid Science, vol. 6, ed. Matijevic, E., Wiley Interscience, 1973, pp. 23–29.

"Perthometer, Surface Texture Parameters," Mahr GMB, Gottingen, Germany ed. Sep. 01, 1999, p. 10.

Patent Abstracts of Japan, vol. 1997, No. 11, Nov. 28, 1997; and JP 09/194674 A, Jul. 29, 1997 (abstract).

* cited by examiner 0.05 μm

CLUSTERED PARTICLE DENTAL FILLERS

FIELD OF THE INVENTION

The invention relates broadly to fillers containing inorganic oxide particles for use in dental materials. Specifically, the fillers of the invention are clusters comprising a plurality of at least two amorphous, inorganic oxides: non-heavy metal oxide particles and a heavy metal oxide. The fillers mixed in a hardenable resin provide radiopaque dental materials that have high strength, good aesthetic character, and good retention of polish.

BACKGROUND

Dental materials generally have unique requirements as compared to the broad spectrum of composite materials. For health reasons, dental materials should be suitable for use in the oral environment. In certain instances, durability of a dental material is important to ensure satisfactory performance. For example, dental work that is performed at dentition locations where mastication forces are generally great, high strength and durability is desirable. In other instances, aesthetic character or quality is highly desired. This is often the case where dental work is performed at locations where a tooth repair or restoration can be seen from a relatively short distance.

Strength of a dental material is typically a result of the addition of fillers. Generally, to provide a dental material possessing greater mechanical strength characteristics, a material is filled or loaded with larger sized particles; i.e. particles that are generally greater than about 0.4 micrometers in diameter. These materials are often referred to as hybrid composites. A disadvantage to these composites, however, is their tendency to lack luster and aesthetic character, especially after exposure to repetitive tooth brushing, a requirement for good oral hygiene.

It is generally desired that the dental restorative material blend well with the surrounding dentition and looks life-like. Aesthetic quality in dental materials is typically achieved by creating material that has tooth-like colors/shades. "Microfills," a certain class of dental materials, tend to have some luster, to better replicate tooth appearance. One example of a "microfill" is commercially available under the trade designation SILUX PLUS (3M Co., St. Paul, Minn.). Microfills, however, generally have less mechanical strength than hybrid composites or "macrofills."

Radiopacity of a dental material can be useful in dentistry. Radiopaque composites can be examined using standard dental X-ray equipment, thereby facilitating long term detection of marginal leakage or caries in tooth tissues adjacent to a cured composite. U.S. Pat. No. 4,503,169 describes a radiopaque, low visual opacity (i.e. translucent) dental composite with non-vitreous zirconia-silica microparticles made by a sol-gel process. The process involves a sintering step followed by milling of the fired filler.

SUMMARY OF THE INVENTION

The invention provides fillers useful in dental materials to provide strong, highly aesthetic, radiopaque materials. Advantageously, the fillers in a hardenable resin provide dental materials that able to retain their polish after repetitive abrasive contact. The filler comprises a substantially amorphous cluster of non-heavy metal oxide particles and a heavy metal oxide, where the cluster has an average diameter of less than about 5 $\mu$m. More preferably the cluster has an average diameter of less than 2 $\mu$m.

"Hardenable" is descriptive of a material that can be cured or solidified e.g., by heating to remove solvent, heating to cause polymerization, chemical crosslinking, radiation-induced polymerization or crosslinking, or the like.

"Non-heavy metal oxide" means any oxide of elements other than those of heavy metals.

"Heavy metal oxide" means an oxide of metals having an atomic number greater than 28.

In one aspect of the invention, the non-heavy metal oxide particles are silica particles.

In another aspect of the invention, the heavy metal oxide is zirconium oxide.

In yet another aspect of the invention, the filler can be loaded into a hardenable resin to provide dental materials having radiopacity, low visual opacity, high mechanical strength and high aesthetic character.

In a further aspect of the invention, the fillers of the invention can be used in dental materials such as adhesives, artificial crowns, anterior or posterior fillings, casting materials, cavity liners, cements, coating compositions, mill blanks, orthodontic devices, restoratives, prostheses, and sealants.

DETAILED DESCRIPTION OF THE PREFERRED EMBODIMENTS

Figure 1:
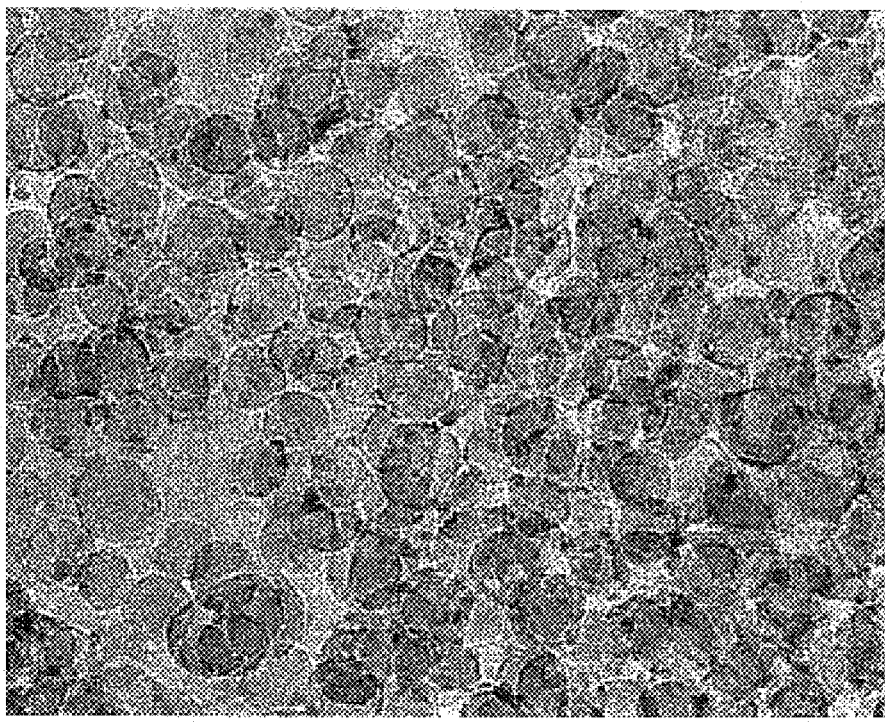
FIG. 1 is a digital image of a TEM (transmission electron micrograph) of a preferred embodiment of a dental material of the invention, taken at 300,000×magnification.

The present invention provides fillers that can be loaded into a dental material to provide materials having radiopacity, high strength, high aesthetic character, and high retention of polish. High aesthetic quality is achieved by providing a dental material that possesses high translucency and good polish. Advantageously, the dental materials of the invention are also preferably able to retain their polish even after exposure to repetitive abrasion.

The filler of the invention can be used in dental materials such as for example, dental adhesives, artificial crowns, anterior or posterior fillings, casting materials, cavity liners, cements, coating compositions, mill blanks, orthodontic devices, restoratives, prostheses, and sealants. In a preferred aspect, the dental material is a dental restorative. The restoratives of the invention can be placed directly in the mouth and cured (hardened) in situ, or alternatively, may be fabricated into a prosthesis outside the mouth and subsequently adhered in place inside the mouth.

It has been found that loading a dental material with fillers that are substantially amorphous and comprised of nanosized particles of a non-heavy metal oxide and a heavy metal oxide imparts a combination of radiopacity and desirable levels of strength, translucency and polish. Surprisingly, placing the fillers of the invention in a hardenable resin provide dental materials that have exceptional capability of retaining their polish, even after being subjected to extended and repetitive abrasion, i.e. toothbrushing. Furthermore, dental materials containing the fillers of the invention have especially desirable handling (rheological) properties in an unhardened state and exceptionally high strength in a hardened state.

Strength can be characterized by mechanical measurements such as compressive strength and diametral tensile strength. High compressive strength in a dental material is advantageous due to the forces exerted by mastication on dental repairs, replacements and restorations. Diametral tensile strength indicates the dental material's ability to withstand compression forces that introduce a tensile stress in the material. Tests for each strength measurement are set out below in the Examples.

The dental materials of the invention preferably have a compressive strength of at least about 35 MPa; more preferably, the materials have a compressive strength of at least about 200 MPa; most preferably, the materials have a compressive strength of at least about 350 MPa.

Hardened dental materials of the invention preferably have a diametral tensile strength of at least about 15 MPa; more preferably at least about 40 MPa; most preferably at least about 60 MPa.

Aesthetic quality of a dental material, although a somewhat subjective characteristic (yet well-understood in the dental industry), can be preferably quantified in one aspect by a visual opacity measurement. Visual opacity is indicative of dental material's level of translucency—low visual opacity is desired so that the hardened dental material will have a life-like luster. The dental materials of the present invention preferably have a visual opacity of about 0.05 to 0.5; more preferably about 0.05 to 0.35; most preferably about 0.05 to 0.25.

Polishability of a dental material also contributes to the aesthetic character and quality of the material. The ability of a dental material to have a glossy finish and life-like luster upon polishing is highly desirable. An even greater benefit is the ability of a hardened material to retain its luster even after repetitive abrasive contact, such as tooth brushing. It has been surprisingly found that materials of the present invention, when made in the preferred embodiment of a dental restorative, have high polishability and are able to retain the polish and luster after repetitive tooth brushing.

To evaluate a hardened, polished dental material's ability to retain its polish, a surface roughness measurement can preferably be determined by subjecting the material to a Toothbrush Abrasion Resistance Test. Using a surface roughness analyzer, commonly referred to as a surface profilometer, the material's roughness (or smoothness) after the Toothbrush Abrasion Resistance Test can be measured. A preferred apparatus to obtain the surface roughness is the WYKO RST PLUS Surface Profiling System (WYKO Corporation, Tuscon, Ariz.), using the test procedure described below in the Test Methods. The surface roughness measurement provides the average variation within the surface by measuring the average height of the profile above and below a central line. After subjecting the dental materials of the invention to the Toothbrush Abrasion Resistance Test, the dental materials preferably have a surface roughness of less than about 0.2 $\mu$m; more preferably less than about 0.15 $\mu$m.

Materials of the invention preferably possess good Theological properties. These properties as well as strength can be enhanced by using surface-modifying agents to treat the surface of the particles. Surface treatment (surface-modification) enhances the dispersibility of the particles and their ability to bind into the matrix.

Practitioners generally desire good handling properties in a dental material, as it often translates to time savings. For example, in dental restorative work, it is desirable that dental materials do not slump because after a practitioner places the material in the mouth and manipulates the material by contouring and feathering, the practitioner generally wants the imparted shape to remain unchanged until the material is hardened. Materials used for restorative work, having a sufficiently high yield stress, generally will not slump; that is, they will not flow under the stress of gravity. The yield stress of a material is the minimum stress required to cause the material to flow, and is described in "Rheology Principles, Measurements, and Applications" by C. W. Macosko, VCH Publishers, Inc., New York, 1994, p. 92. If the stress due to gravity is below the yield stress of the material, then the material will not flow. The stress due to gravity, however, will depend on the mass of dental material being placed as well as the shape.

"Contouring" refers to the process of shaping a material (using dental instruments) so that it resembles the natural dental anatomy. For easy contouring, materials should have a sufficiently high viscosity that they maintain their shape after manipulation with a dental instrument, and yet the viscosity should not be so high that it is difficult to shape the material. "Feathering" refers to the process of reducing the dental material to a thin film in order to blend the material into the natural dentition. This is done with a dental instrument at the margin of the manipulated material and the natural dentition. It is also desirable that the dental material not stick to placement instruments, to minimize further alteration of the shape or surface topography.

In a preferred embodiment where the dental material of the invention is a restorative, the dental material preferably has little to no slump, yet easily adapts to, for example, a cavity preparation, and is easily contoured and feathered. Preferably, the dental materials of the invention do not stick to placement instruments, and are advantageously, overall, fast and easy to use in dental procedures such as, for example, restoring tooth structure.

The fillers of the invention comprise a substantially amorphous cluster of non-heavy metal oxide particles and heavy metal oxide. As explained below, the heavy metal oxide can be present in the cluster as individual particles, a coating on the non-heavy metal oxide particles, or as a region in non-heavy metal oxide particles. Regardless of the form in which the heavy metal oxide is found, the cluster of non-heavy metal oxide particles and heavy metal oxide is substantially amorphous.

A "cluster" refers to the nature of the association among the non-heavy metal oxide particles present in the cluster. Typically, the non-heavy metal oxide particles are associated by relatively weak intermolecular forces that cause the non-heavy metal oxide particles to clump together, even when dispersed in a hardenable resin for a dental material. To the extent that the heavy metal oxide is present in the cluster as particles, the heavy metal oxide particles display a similar association to each other and to the non-heavy metal oxide particles.

By "substantially amorphous" it is meant that the clusters are essentially free of crystalline structure. Absence of crystallinity (or presence of amorphous phases) is preferably determined by a procedure that provides a Crystallinity Index, as described below in the Test Methods. The Crystallinity Index characterizes the extent a material is crystalline or amorphous, whereby a value of 1.0 is indicative of a fully crystalline structure, and a value near zero indicates presence of amorphous phase only. The fillers of the invention preferably have an index of less than about 0.1; more preferably less than about 0.05.

The fillers of the invention are preferably not fully densified. The term "fully dense," as used herein, is descriptive of a particle that is near theoretical density, having substantially no open porosity detectable by standard analytical techniques such as the B.E.T. nitrogen technique (based upon adsorption of $N_2$ molecules from a gas with which a specimen is contacted). Such measurements yield data on the surface area per unit weight of a sample (e.g. $m^2/g$) which can be compared to the surface area per unit weight for a mass of perfect microspheres of the same size to detect open porosity. Such measurements may be made on a Quantasorb apparatus made by Quantachrome Corporation of Syossett, N.Y. Density measurements may be made using an air, helium or water pycnometer.

As discussed more fully hereinbelow, the fillers of the invention are often manufactured in a process that includes heat treatment. The surface area of the filler after heat treatment compared to its surface area before heat treatment, is preferably quite high. The ratio of the surface area after heat treatment compared to the surface area before heat treatment is preferably greater than about 50%, more preferably greater than about 80%.

Suitable non-heavy metal oxide particles that can be used in the dental materials of the invention include, for example, silica, calcium phosphate, titanium oxide, feldspathic materials, aluminum oxide, and the like. Preferably, the non-metallic oxide particles are silica that are present in the dental material in various forms, including for example, fumed silica, colloidal silica, or aggregated silica particles.

The non-heavy metal oxide particles used in the dental materials of the invention preferably have an average diameter of less than about 100 nm; more preferably, the particles are less than about 50 nm in average diameter. These measurements are preferably based on a TEM (transmission electron microscopy) method, whereby a population of particles such as what is show in FIG. 1, is analyzed to obtain an average particle diameter. A preferred method for measuring the particle diameter is set out below, in the Test Methods section.

The non-heavy metal particles used in the dental materials of the present invention are preferably substantially spherical and substantially non-porous. Although the silica is preferably essentially pure, it may contain small amounts of stabilizing ion such as ammonium and alkaline metal ions.

Preferred nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols which can be used in preparing the fillers of the invention are available commercially having different colloid sizes, see Surface & Colloid Science, Vol. 6, ed. Matijevic, E., Wiley Interscience, 1973. Preferred silica sols for use making the fillers of the invention are those which are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E. I. Dupont de Nemours & Co. or Nalco 2326 from Nalco Chemical Co.).

Preferably, the silica particles in the sol have an average particle diameter of about 5–100 nm, more preferably 10–50 nm, most preferably, 12–40 nm. A particularly preferred silica sol is NALCO 1042.

One or more amorphous heavy metal oxides are present in the fillers of the invention to impart radiopacity to a dental material having an effective amount of the fillers loaded in a hardenable resin. As used herein, "radiopacity" describes the ability of a hardened dental material to be distinguished from tooth structure using standard dental X-ray equipment in the conventional manner. Radiopacity in a dental material is advantageous in certain instances where X-rays are used to diagnose a dental condition. For example, a radiopaque material would allow the detection of secondary caries that may have formed in the tooth tissue surrounding a filling. The desired degree of radiopacity can be varied, depending upon the particular application and the expectations of the practitioner evaluating the X-ray film.

Heavy metal oxides are oxides of metals having an atomic number greater than 28. The heavy metal oxide should be chosen such that undesirable colors or shading are not imparted to the hardened resin in which it is dispersed. For example, iron and cobalt would not be favored, as they impart dark and contrasting colors to the neutral tooth color of the dental material. More preferably, the heavy metal oxide is an oxide of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Most preferably, the oxides of heavy metals having an atomic number greater than 30, but less than 72. Particularly preferred radiopacifying metal oxides include lanthanum oxide, zinc oxide, tin oxide, zirconium oxide, yttrium oxide, ytterbium oxide, barium oxide, strontium oxide, cerium oxide, and combinations thereof.

The heavy metal oxide components, as well as other additives, may be included in the dental materials of the invention in various forms, including for example, particles on the surface of the non-heavy metal oxide or amongst the non-heavy metal oxide particles, or as a coating on at least a portion of the surface of a non-heavy metal oxide particle. Alternatively, the heavy metal oxide may be present in the non-heavy metal oxide particle as a solid solution (e.g., continuous glass) or a precipitate (a second phase).

Preferably, the heavy metal oxide is provided in the form of particles. The heavy metal oxide particles preferably have an average diameter of less than about 100 nm. More preferably, the particles are less than about 50 nm; most preferably less than about 10 nm in average diameter. The heavy metal oxide particles may be aggregated. If so, it is preferred that the aggregated particles are less than about 100 nm, and more preferably are less than about 50 nm in average diameter.

The heavy metal oxide precursor useful in making the heavy metal oxide component used in the fillers and materials of the invention can be organic or inorganic acid or water soluble salts, such as the heavy metal salts of aliphatic mono or dicarboxylic acids (e.g. formic, acetic, oxalic, citric, tartaric, and lactic acids). Preferred heavy metal compounds contain zirconium. Zirconyl acetate compounds are particularly preferred. Useful inorganic zirconium compounds which can be used are zirconium oxynitrate and zirconium oxychloride. See U.S. Pat. No. 3,709,706, Column 4, line 61-Column 5, line 5 for further details on zirconia sources which can be used in this invention. A particularly preferred zirconyl acetate is available from MEI (Magnesium Elektron, Flemington, N.J.).

Incorporation of the fillers of the invention into a hardenable resin can be facilitated by surface treating the fillers. Surface treatment enhances stabilization of the fillers in the hardenable resin to provide a stable dispersion of the filler in the resin. "Stable", as used herein, means a dental material in which the fillers do not settle or agglomerate after standing for a period of time, such as about 24 hours, under standard ambient conditions—e.g. room temperature (about 20–22° C.), atmospheric pressure, and no extreme electromagnetic forces. Preferably, the surface-treatment stabilizes the filler so that they will be well dispersed in the hardenable resin and results in a substantially homogeneous composition. Furthermore, it is preferred that the filler be modified over at least a portion of its surface with a surface treatment agent so that the stabilized particle can copolymerize or otherwise react with the hardenable resin during curing.

The fillers of the present invention are preferably treated with a resin-compatibilizing surface treatment agent. Particularly preferred surface treatment or surface modifying agents include silane treatment agents capable of polymerizing with a resin. Preferred silane treatment agent include γ-methacryloxylpropyltrimethoxysilane, available commercially under the trade designation A-174, available commercially from Witco OSi Specialties (Danbury, Conn.) and γ-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic function subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, aryl polyethers, alkyl, hydroxy alkyl, hydroxy aryl, or amino alkyl functional silanes.

The fillers of the invention can be incorporated into a hardenable resin to provide useful dental materials. Dental materials of the present invention can be chemically curable, heat curable or light curable compositions. Light curable materials should have an appropriate initiator system. Chemically curable materials can be auto-cure (e.g. via redox initiators). Alternatively, the materials of the invention can be hardened by a combination of auto- and light-cure.

To achieve good translucency, it is desirable to minimize the scattering of light as it passes through the material. This is preferably accomplished by matching the average refractive index of the filler and the resin. The resins useful for the dental materials of the invention are preferably and generally thermosetting resins capable of being hardened to form a polymer network such as, for example, acrylate resins, methacrylate resins, epoxy resins, vinyl resins or mixtures thereof. Preferably, the hardenable resin is made from one or more matrix-forming oligomer, monomer, or polymer, or blends thereof.

In a preferred embodiment where the dental material of the invention is a dental composite, polymerizable resins suitable for use include hardenable organic resins having sufficient strength, hydrolytic stability, and non-toxicity to render them suitable for use in the oral environment. Examples of such resins include acrylate, methacrylate, urethane, carbamoylsiocyanurate and epoxy resins, e.g., those shown in U.S. Pat. Nos. 3,066,112, 3,539,533, 3,629,187, 3,709,866, 3,751,399, 3,766,132, 3,860,556, 4,002,669, 4,115,346, 4,259,117, 4,292,029, 4,308,190, 4,327,014, 4,379,695, 4,387,240 and 4,404,150, and mixtures and derivatives thereof.

One class of preferred hardenable resins are materials having free radically active functional groups and include monomers, oligomers, and polymers having one or more ethylenically unsaturated groups. Alternatively, the hardenable resin can be a material from the class of resins that include cationically active functional groups. In another alternative, a mixture of hardenable resins that include both cationically curable and free radically curable resins may be used for the dental materials of the invention.

In the class of hardenable resins having free radically active functional groups, suitable materials for use in the invention contain at least one ethylenically unsaturated bond, and are capable of undergoing addition polymerization. Such free radically polymerizable materials include mono-, di- or poly- acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol A ("Bis-GMA"), bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200–500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyladipate and divinylphthalate. Mixtures of two or more of these free radically polymerizable materials can be used if desired.

For free radical polymerization (hardening), an initiation system can be selected from systems which initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically an be capable of generating free radicals for addition polymerization upon exposure to light energy having a wavelength between 200 and 800 nm.

A variety of visible or near-IR photoinitiator systems may be used for photopolymerization of free-radically polymerizable materials useful in the invention. For example, in free radical polymerization (hardening), a photoinitiation system can be selected from systems which initiate polymerization via a two component system of an amine and an α-diketone as described in U.S. Pat. No. 4,071,424, which is herein incorporated by reference. Alternatively, the resin can be combined with a three component or ternary photoinitiator system such as described in U.S. Pat. No. 5,545,676 which is incorporated herein by reference.

In the ternary photoinitiator system, the first component is an iodonium salt, i.e., a diaryliodonium salt. The iodonium salt is preferably soluble in the monomer and shelf-stable (i.e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. Nos. 3,729,313, 3,741,769, 3,808,006, 4,250,053 and 4,394,403, the iodonium salt disclosures of which are incorporated herein by reference. The iodonium salt can be a simple salt (e.g., containing an anion such as $Cl^-$, $Br^-$, $I^-$ or $C_4H_5SO_3^-$) or a metal complex salt (e.g., containing $SbF_5OH^-$ or $AsF_6^-$). Mixtures of iodonium salts can be used if desired. Preferred iodonium salts include diphenyliodonium salts such as diphenyliodonium chloride, diphenyliodonium hexafluorophosphate and diphenyliodonium tetrafluoroborate.

The second component in a ternary photoinitiator system is a sensitizer. The sensitizer desirably is soluble in the monomer, and is capable of light absorption somewhere within the range of wavelengths of greater than 400 to 1200 nanometers, more preferably greater than 400 to 700 nanometers and most preferably greater than 400 to about 600 nanometers. The sensitizer may also be capable of sensitizing 2-methyl-4,6-bis(trichloromethyl)-s-triazine, using the test procedure described in U.S. Pat. No. 3,729,313, which is incorporated herein by reference. Preferably, in addition to passing this test, a sensitizer is also selected based in part upon shelf stability considerations. Accordingly, selection of a particular sensitizer may depend to some extent upon the particular monomer, oligomer or polymer, iodonium salt and donor chosen.

Suitable sensitizers can include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring high sensitivity, it is preferred to employ a sensitizer containing a julolidinyl moiety. For applications requiring deep cure (e.g., cure of highly-filled composites), it is preferred to employ sensitizers having an extinction coefficient below about 1000, more preferably below about 100, at the desired wavelength of irradiation for photopolymerization. Alternatively, dyes that exhibit reduction in light absorption at the excitation wavelength upon irradiation can be used.

For example, a preferred class of ketone sensitizers has the formula:

where X is CO or $CR^5 R^6$, where $R^5$ and $R^6$ can be the same or different, and can be hydrogen, alkyl, alkaryl or aralkyl, b is zero or one, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2'-, 4,4'- or 2,4'-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3,3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, and the like.

The third component of a ternary initiator system is a donor. Preferred donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676, which is incorporated herein by reference.

Alternatively, free-radical initiators useful in the invention include the class of acylphosphine oxides, as described in European Patent Application No. 173567, U.S. Pat. No. 4,737,593 and United Kingdom Pat. No. GB 2,310,855. Such acylphosphine oxides are of the general formula

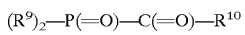

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S—, O—, or N— containing five- or six-membered heterocyclic group, or a —Z—C(=O)—P(=O)—$(R^9)_2$ group, wherein Z represents a divalent hydrocarbyl group such as alkylene or phenylene having from 2 to 6 carbon atoms.

Preferred acylphosphine oxides useful in the invention are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is bis(2,4,6-trimethylbenzoyl)phenyl phosphine oxide (IRGACURE™ 819, Ciba Specialty Chemicals, Tarrytown, N.Y.).

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. The initiator can be employed in catalytically-effective amounts, such as from about 0.1 to about 5 weight percent, based on the weight of ethylenically-unsaturated compound present, of the acylphosphine oxide plus from about 0.1 to about 5 weight percent, based on the weight of ethylenically-unsaturated compound present, of the tertiary amine.

Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis($\eta^5$-2,4-cyclopentadien-1-yl)-bis(2,6-difluoro-3-(1H-pyrrol-1-yl)phenyl)titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

Another free-radical initiator system that can alternatively be used in the dental materials of the invention includes the class of ionic dye—counterion complex initiators comprising a borate anion and a complementary cationic dye.

Borate salt photoinitiators are described, for example, in U.S. Pat. Nos. 4,772,530, 4,954,414, 4,874,450, 5,055,372, and 5,057,393, the disclosures of which are incorporated herein by reference. Borate anions useful in these photoinitiators generally can be of the formula $$R^1R^2R^3R^4B^-$$

wherein $R^1$, $R^2$, $R^3$, and $R^4$ independently can be alkyl, aryl, alkaryl, allyl, aralkyl, alkenyl, alkynyl, alicyclic and saturated or unsaturated heterocyclic groups. Preferably, $R^2$, $R^3$, and $R^4$ are aryl groups and more preferably phenyl groups, and $R^1$ is an alkyl group and more preferably a secondary alkyl group.

Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodamine, and azomethine dyes. Specific examples of useful cationic dyes include Methylene Blue, Safranine O, and Malachite Green. Quaternary ammonium groups useful as counterions can be trimethylcetylammonium, cetylpyridinium, and tetramethylammonium. Other organophilic cations can include pyridinium, phosphonium, and sulfonium. Photosensitive transition metal coordination complexes that may be used include complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri(2-pyridyl-s-triazine) and related ligands.

Yet another alternative class of initiators capable of initiating polymerization of free radically active functional groups includes conventional chemical initiator systems such as a combination of a peroxide and an amine. These initiators, which rely upon a thermal redox reaction, are often referred to as "auto-cure catalysts." They are typically supplied as two-part systems in which the reactants are stored apart from each other and then combined immediately prior to use.

In a further alternative, heat may be used to initiate the hardening, or polymerization, of free radically active groups. Examples of heat sources suitable for the dental materials of the invention include inductive, convective, and radiant. Thermal sources should be capable of generating temperatures of at least 40° C. to 15° C. under normal conditions or at elevated pressure. This procedure is preferred for initiating polymerization of materials occurring outside of the oral environment.

Yet another alternative class of initiators capable of initiating polymerization of free radically active functional groups that are useful for the dental materials of the invention are those that include free radical-generating thermal initiators. Examples include peroxides such as, for example, benzoyl peroxide and lauryl peroxide, and azo compounds such as, for example, 2,2-azobis-isobutyronitrile (AIBN).

An alternative class of hardenable resins useful in the dental materials of the invention may include cationically active functional groups. Materials having cationically active functional groups include cationically polymerizable epoxy resins, vinyl ethers, oxetanes, spiro-orthocarbonates, spiro-orthoesters, and the like.

Preferred materials having cationically active functional groups are epoxy resins. Such materials are organic compounds having an oxirane ring, i.e., a group of the formula

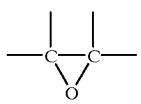

which is polymerizable by ring opening. These materials include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexane oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl)adipate. For a more detailed list of useful epoxides of this nature, reference is made to the U.S. Pat. No. 3,117,099, which is incorporated herein by reference.

Further epoxy-containing materials which are useful in the compositions of this invention include glycidyl ether monomers of the formula

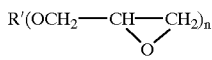

where R' is alkyl or aryl and n is an integer of 1 to 6. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)-propane). Further examples of epoxides of this type are described in U.S. Pat. No. 3,018,262, which is incorporated herein by reference, and in "Handbook of Epoxy Resins" by Lee and Neville, McGraw-Hill Book Co., New York (1967).

Still other epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins are well known and contain such epoxides as epichlorohydrins, alkylene oxides, e.g., propylene oxide, styrene oxide; alkenyl oxides, e.g., butadiene oxide; glycidyl esters, e.g., ethyl glycidate.

Blends of various epoxy-containing materials are also contemplated. Examples of such blends include two or more weight average molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical natures, such as aliphatic and aromatic, or functionalities, such as polar and non-polar.

There are a host of commercially available epoxy resins which can be used in this invention. In particular, epoxides which are readily available include octadecylene oxide, epichlorohydrin, styrene oxide, vinylcyclohexene oxide, glycidol, glycidyl methacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexene carboxylate (e.g., "ERL-4221" or "CYRACURE UVR 6110" or "UVR 6105" from Union Carbide Corp.), 3,4-epoxy-6-methylcyclohexylmethyl-3,4-epoxy-6-methylcyclohexene carboxylate (e.g., "ERL-4201" from Union Carbide Corp.), bis(3,4-epoxy-6-methylcyclohexylmethyl)adipate (e.g., "ERL-4289" from Union Carbide Corp.), bis(2,3-epoxycyclopentyl)ether (e.g., "ERL-0400" from Union Carbide Corp.), aliphatic epoxy modified from polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from Dow Chemical Co.), 1,4-butanediol diglycidyl ether of phenolformaldehyde novolak (e.g., "DEN-431" and "DEN-438" from Dow Chemical Co.), and resorcinol diglycidyl ether (e.g., "Kopoxite" from Koppers Company, Inc.), bis(3,4-epoxycyclohexyl)adipate (e.g., "ERL-4299" or "UVR-6128", from Union Carbide Corp.), 2-(3,4-epoxycyclohexyl-5,5-spiro-3,4-epoxy) cyclohexane-metadioxane (e.g., "ERL-4234" from Union Carbide Corp.), vinylcyclohexene monoxide 1,2-epoxyhexadecane (e.g., "UVR-6216" from Union Carbide Corp.), alkyl glycidyl ethers such as alkyl $C_8$–$C_{10}$ glycidyl ether (e.g., "HELOXY Modifier 7" from Shell Chemical Co.), alkyl $C_{12}$–$C_{14}$ glycidyl ether (e.g., "HELOXY Modifier 8" from Shell Chemical Co.), butyl glycidyl ether (e.g., HELOXY Modifier 61" from Shell Chemical Co.), cresyl glycidyl ether (e.g., "HELOXY Modifier 62" from Shell Chemical Co.), p-ter butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1138" or "GY-281" from Ciba-Geigy Corp.), 9,9-bis[4-(2,3-epoxypropoxy)phenyl]fluorenone (e.g., "Epon 1079" from Shell Chemical Co.).

It is also within the scope of this invention to use one or more epoxy resins blended together. The different kinds of resins can be present in any proportion.

Optionally, monohydroxy- and polyhydroxy-alcohols may be added to the curable compositions of the invention, as chain-extenders for the epoxy resin. The hydroxyl-containing material used in the present invention can be any organic material having hydroxyl functionality of at least 1, and preferably at least 2.

Preferably the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, ie., from about 32 to 200, intermediate molecular weight, i.e., from about 200 to 10,000, or high molecular weight, i.e., above about 10,000. As used herein, all molecular weights are weight average molecular weights.

The hydroxyl-containing material can optionally contain other functionalities that do not substantially interfere with cationic cure at room temperature. Thus, the hydroxyl-containing materials can be nonaromatic in nature or can contain aromatic functionality. The hydroxyl-containing material can optionally contain heteroatoms in the backbone of the molecule, such as nitrogen, oxygen, sulfur, and the like, provided that the ultimate hydroxyl-containing material does not substantially interfere with cationic cure at room temperature. The hydroxyl-containing material can, for example, be selected from naturally occurring or synthetically prepared cellulosic materials. Of course, the hydroxyl-containing material is also substantially free of groups which may be thermally or photolytically unstable; that is, the material will not decompose or liberate volatile components at temperatures below about 100° C. or in the presence of actinic light which may be encountered during the desired curing conditions for the photocopolymerizable composition. Useful hydroxyl-containing materials are described, for example, in U.S. Pat. No. 5,856,373, which is incorporated herein by reference.

The amount of hydroxyl-containing organic material used in the compositions of the invention may vary over broad ranges, depending upon factors such as the compatibility of the hydroxyl-containing material with the epoxide, the equivalent weight and functionality of the hydroxyl-containing material, the physical properties desired in the final cured composition, the desired speed of photocure, and the like.

Blends of various hydroxyl-containing materials may be useful in the dental materials of the invention. Examples of such blends include two or more molecular weight distributions of hydroxyl-containing compounds, such as low molecular weight (below 200), intermediate molecular weight (about 200 to 10,000) and higher molecular weight (above about 10,000). Alternatively or additionally, the hydroxyl-containing material can contain a blend of hydroxyl-containing materials having different chemical natures, such as aliphatic and aromatic, or functionalities, such as polar and non-polar. As an additional example, one may use mixtures of two or more poly-functional hydroxy materials or one or more mono-functional hydroxy materials with poly-functional hydroxy materials.

For hardening resins comprising cationically active functional groups, an initiation system can be selected from systems which initiate polymerization via radiation, heat, or redox/auto-cure chemical reaction. For example, epoxy polymerization may be accomplished by the use of thermal curing agents, such as anhydrides or amines. A particularly useful example of an anhydride curing agent would be cis-1,2-cyclohexanedicarboxylic anhydride.

Alternatively and preferably, initiation systems for resins comprising cationically active functional groups are those that are photoactivated. The broad class of cationic photoactive groups recognized in the catalyst and photoinitiator industries may be used in the practice of the present invention. Photoactive cationic nuclei, photoactive cationic moieties, and photoactive cationic organic compounds are art recognized classes of materials as exemplified by U.S. Pat. Nos. 4,250,311; 3,708,296; 4,069,055; 4,216,288; 5,084,586; 5,124,417; 4,985,340, 5,089,536, and 5,856,373, each of which is incorporated herein by reference.

The cationically-curable materials can be combined with a three component or ternary photoinitiator system, as described above. Three component initiator systems are also described in U.S. Pat. Nos. 5,998,495 and 6,025,406, each of which is incorporated herein by reference.

For hardening cationically curable resins, examples of useful aromatic iodonium complex salts (i.e. the first component of the ternary photoinitiator system) include: diphenyliodonium tetrafluoroborate; di(4-methylphenyl)iodonium tetrafluoroborate; phenyl-4-methylphenyliodonium tetrafluoroborate; di(4-heptylphenyl)iodonium tetrafluoroborate; di(3-nitrophenyl)iodonium hexafluorophosphate; di(4-chlorophenyl)iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl)iodonium tetrafluoroborate; phenyl-2-thienyliodoniun hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl)iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; and diphenyliodonium hexafluoroantimonate (DPISbF$_6$).

Of the aromatic iodonium complex salts which are suitable for use in the compositions of the invention diaryliodonium hexafluorophosphate and diaryliodonium hexafluoroantimonate are among the preferred salts. These salts are preferred because, in general, they promote faster reaction, and are more soluble in inert organic solvents than are other aromatic iodonium salts of complex ions.

As mentioned above, the second and third component of the ternary photoinitiator system is a sensitizer and an electron donor, respectively. The sensitizers useful in cationic polymerization of the dental materials of the invention are those that are described above for the free-radically cured materials. Similarly, the electron donor useful for cationic polymerization of the materials of the invention include those that are described above for the free-radically cured materials. However, in the case of cationically cured materials, the electron donor preferably meets the requirements set forth in U.S. Pat. Nos. 5,998,495 and 6,025,406, each of which is incorporated herein by reference, and are soluble in the polymerizable composition. The donor can also be selected in consideration of other factors, such as shelf stability and the nature of the polymerizable materials, iodonum salt and sensitizer chosen. A class of donor compounds that may be useful in the inventive systems may be selected from some of the donors described in U.S. Pat. No. 5,545,676.

The donor is typically an alkyl aromatic polyether or an N-alkyl arylamino compound wherein the aryl group is substituted by one or more electron withdrawing groups. Examples of suitable electron withdrawing groups include carboxylic acid, carboxylic acid ester, ketone, aldehyde, sulfonic acid, sulfonate and nitrile groups.

A preferred group of N-alkyl arylamino donor compounds is described by the following structural formula:

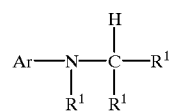

wherein each $R^1$ is independently H, $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, COOH, COOC$_{1-18}$ alkyl, (C$_{1-18}$ alkyl)$_{0-1}$—CO—C$_{1-18}$ alkyl, SO$_3$R$^2$, CN or an aryl group that is optionally substituted by one or more electron withdrawing groups, or the $R^1$ groups may be joined to form a ring; and Ar is aryl that is substituted by one or more electron withdrawing groups. Suitable electron withdrawing groups include —COOH, —COOR$^2$, —SO$_3$R$^2$, —CN, —CO—C$_{1-18}$ alkyl and —C(O)H groups, wherein R$^2$ can be a $C_{1-18}$ straight-chain, branched, or cyclic alkyl group.

A preferred group of aryl alkyl polyethers has the following structural formula:

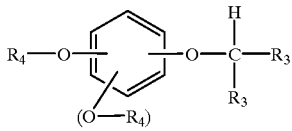

wherein n=1–3 each $R^3$ is independently H or $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, substituted aryl, —COOH, —COOC$_{1-18}$ alkyl, —($C_{1-18}$ alkyl)$_{0-1}$—COH, —($C_{1-18}$ alkyl)$_{0-1}$—CO—$C_{1-18}$ alkyl, —CO—$C_{1-18}$ alkyl, —C(O)H or —$C_{2-18}$ alkenyl groups and each $R^4$ can be $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, substituted aryl, —COOH, —COOC$_{1-18}$ alkyl, —($C_{1-18}$ alkyl)$_{0-1}$—COH, —($C_{1-18}$ alkyl)$_{0-1}$—CO—$C_{1-18}$ alkyl, —CO—$C_{1-18}$ alkyl, —C(O)H or —$C_{2-18}$ alkenyl groups.

In each of the above formulas the alkyl groups can be straight-chain or branched, and the cycloalkyl group preferably has 3 to 6 ring carbon atoms but may have additional alkyl substitution up to the specified number of carbon atoms. The aryl groups may be carbocyclic or heterocyclic aryl, but are preferably carbocyclic and more preferably phenyl rings.

Preferred donor compounds include 4-dimethylaminobenzoic acid, ethyl 4-dimethylaminobenzoate, 3-dimethylaminobenzoic acid, 4-dimethylaminobenzoin, 4-dimethylaminobenzaldehyde, 4-dimethylaminobenzonitrile and 1,2,4-trimethoxybenzene.

An alternative photoinitiator system for cationic polymerizations includes the use of organometallic complex cations essentially free of metal hydride or metal alkyl functionality selected from those described in U.S. Pat. No. 4,985,340, and such description is incorporated herein by reference and has the formula:

$$[(L^1)(L^2)M]^{+q} \qquad (1)$$

wherein

M represents a metal selected from the group consisting of Cr, Mo, W, Mn, Re, Fe, Ru, Os, Co, Rh, Ir, Pd, Pt and Ni, preferably Cr, Mo, W, Mn, Fe, Ru, Co, Pd, and Ni; and most preferably Mn and Fe;

$L^1$ represents 1 or 2 cyclic, polyunsaturated ligands that can be the same or different ligand selected from the group consisting of substituted and unsubstituted cyclopentadienyl, cyclohexadienyl, and cycloheptatrienyl, cycloheptatriene, cyclooctatetraene, heterocyclic compounds and aromatic compounds selected from substituted or unsubstituted arene compounds and compounds having 2 to 4 fused rings, and units of polymers, e.g., a phenyl group of polystyrene, poly(styrene-co-butadiene), poly(styrene-co-methyl methacrylate), poly (a-methylstyrene), and the like; a cyclopentadiene group of poly(vinylcyclopentadiene); a pyridine group of poly(vinylpyridine), and the like, each capable of contributing 3 to 8 electrons to the valence shell of M;

$L^2$ represents none, or 1 to 3 nonanionic ligands contributing an even number of electrons that can be the same or different ligand selected from the group of carbon monoxide, ketones, olefins, ethers, nitrosonium, phosphines, phosphites, and related derivatives of arsenic and antimony, organonitriles, amines, alkynes, isonitriles, dinitrogen, with the proviso that the total electronic charge contributed to M results in a net residual positive charge of q to the complex;

q is an integer having a value of 1 or 2, the residual charge of the complex cation.

Organometallic salts are known in the art and can be prepared as described in, for example, EPO No. 094,914 and U.S. Pat. Nos. 5,089,536, 4,868,288, and 5,073,476, and such descriptions are incorporated herein by reference.

Examples of preferred cations include:

diphenyliodonium, ditolyliodonium, didodecylphenyliodonium, (4-octyloxyphenyl)phenyliodonium, and bis(methoxyphenyl)iodonium;

triphenylsulfonium, diphenyl-4-thiophenoxyphenylsulfonium, and 1,4-phenylene-bis(diphenylsufonium);

bis($\eta^5$-cyclopentadienyl)iron(1+), bis($\eta^5$-methylcyclopentadienyl)iron (1+), ($\eta^5$-cyclopentadienyl)($\eta^5$-methylcyclopentadienyl)iron (1+), and bis($\eta^5$-trimethylsilylcyclopentadienyl)iron (1+);

bis($\eta^6$-xylenes)iron (2+), bis($\eta^6$-mesitylene)iron (2+), bis($\eta^6$-durene)iron (2+), bis($\eta^6$-pentamethylbenzene)iron (2+), and bis($\eta^6$-dodecylbenzene) iron (2+);

($\eta^5$-cyclopentadienyl)($\eta^6$-xylenes)iron(1+), commonly abbreviated as (CpFeXy)(1+), ($\eta^5$-cyclopentadienyl)($\eta^6$-toluene)iron(1+), ($\eta^5$-cyclopentadienyl)($\eta^6$-mesitylene)iron(1+), ($\eta^5$-cyclopentadienyl)($\eta^6$-pyrene)iron(1+), ($\eta^5$-cyclopentadienyl)($\eta^6$-naphthalene)iron(1+), and ($\eta^5$-cyclopentadienyl)($\eta^6$-dodecylphenyl)iron(1+).

Alternatively, hardenable resins useful for the invention may have both cationically active and free radically active functional groups contained in a single molecule. Such molecules may be obtained, for example, by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the "Cyclomer" series, such as Cyclomer M-100, M-101, or A-200 available from Daicel Chemical, Japan, and Ebecryl-3605 available from Radeure Specialties.

The photoinitiator compounds are preferably provided in the dental materials of the invention in an amount effective to initiate or enhance the rate of cure or hardening of the resin system. Photopolymerizable compositions useful in the invention are prepared by simply admixing, under "safe light" conditions, the components as described above. Suitable inert solvents may be employed if desired when effecting this mixture. Any solvent may be used which does not react appreciably with the components of the inventive compositions. Examples of suitable solvents include acetone, dichloromethane, and acetonitrile. A liquid material to be polymerized may be used as a solvent for another liquid or solid material to be polymerized. Solventless compositions can be prepared by simply dissolving an aromatic iodonium complex salt and sensitizer in an epoxy resin polyol mixture with or without the use of mild heating to facilitate dissolution.

As noted above, the clusters of the invention are substantially amorphous. The provision of substantially amorphous clusters may be facilitated by the appropriate selection of heat treatments, for example, by maintaining the temperature of a heat treatment at a level that is sufficiently low that essentially no crystallinity is found after milling.

The clusters are prepared from a suitable sol and one or more oxygen containing heavy metal compound solution(s) precursors which may be salts, sols, solutions, or nano-sized particles; of these, sols are preferred. For purposes of this invention, a sol is defined as a stable dispersion of colloidal solid particles within a liquid. The solid particles are typically denser than the surrounding liquid and small enough so that the dispersion forces are greater than the gravitational force. In addition, the particles are of a size small enough so that they generally do not refract visible light. Judicious choice of the precursor sols leads to desired degree of visual opacity, strength etc. Factors that will guide the choice of the sol depends on the combination of the following properties: a) the average size of the individual particles, which is preferably less than about 100 nm in diameter, b) the acidity: the pH of the sol should be preferably be below about 6 and more preferably below about 4, and c) the sol should be free of impurities that cause undue aggregation (during the filler preparation process) of the individual discrete particles, during the subsequent steps such as spray drying or calcining, into larger size particles that cannot be easily dispersed or commuted and hence decrease the translucency and polishability. If the starting sol is basic, it should be acidified e.g. by addition of nitric or other suitable acid to decrease the pH. However choosing a basic starting sol is less desirable since it requires an additional step and may lead to the introduction of undesired impurities. Typical impurities that are preferably avoided are metal salts, particularly salts of alkaline metals e.g. sodium.

The non-heavy metal sol and heavy metal oxide precursors are mixed together preferably at a molar ratio to match the index of refraction of the hardenable resin. This imparts a low and desirable visual opacity. Preferably, the molar ratio ranges of non-heavy metal oxide ("non-HMO") to heavy metal oxide ("HMO"), expressed as non-HMO:HMO is about 0.5:1 to about 10:1, more preferably about 3:1 to about 9:1, and most preferable about 4:1 to 7:1. In a preferred embodiment where the clusters of the invention contain silica and zirconium containing compounds, the method of preparation starts with a mixture of silica sol and zirconyl acetate, at about a 5.5:1 molar ratio.

Prior to mixing the non-heavy metal oxide sol with the heavy metal oxide precursor, the pH of the non-heavy metal oxide sol is preferably reduced to provide an acidic solution having a pH of about 1.5 to about 4.0.

The non-heavy metal oxide sol is then slowly mixed with the solution containing the heavy metal oxide precursor and vigorously agitated. Strong agitation is preferably performed throughout the blending process. The solution is then dried to remove the water and other volatile components. Drying can be accomplished in various ways, including for example, tray drying, fluidized bed and spray drying. In the preferred method where zirconyl acetate is used, drying by means of spray drying using a 120° C. outlet temperature removes the water and a small amount of acetic acid.

The resulting dried material is preferably made up of small substantially spherical particles as well as broken hollow spheres. These fragments are then batch calcined to further remove residual organics. The removal of the residual organics allows the filler to be come more brittle, which results in more efficient particle size reduction. During calcining, the soak temperature is preferably set at about 200° C. to about 800° C., more preferably about 300° C. to about 600° C. Soaking is performed for about 0.5 hours to about 8 hours, depending on the amount of material being calcined. It is preferred that the soak time of the calcine step be such that a plateaued surface area is obtained. It is preferred that the time and temperature be chosen such that the resulting filler is white in color, free from black, grey, or amber colored particles, as determined by visual inspection.

The calcined material is then preferably milled to a median particle size of less than about 5 microns, preferably less than 2 microns (on a volumetric basis), as determined using a Sedigraph 5100 (Micrometrics, Norcross, Ga.). The particle size determination is performed by first obtaining the specific density of the filler using an Accuracy 1330 Pycometer (Micrometrics, Norcross, Ga.) described in the Test Methods. Milling can be accomplished by various methods including for example, stirred milling, vibratory milling, fluid energy milling, jet milling and ball milling. Ball milling is the preferred method.

The resulting fillers are weakly-bound aggregates or clusters of discrete primary particles which are clustered together as seen in FIG. 1, a TEM of the materials of the invention. Referring to FIG. 1, a portion of a TEM showing a preferred embodiment of a filler of the invention, comprising a silica particles and zirconia particles in a resin.

Dental materials of the invention preferably contain about 35 wt % to about 95 wt % of the fillers of the invention, based on the total weight of the hardenable resin. More preferably, the fillers are present in the dental material at concentrations of about 50 wt % to about 85 wt %.

The dental materials of the present invention may optionally comprise additional adjuvants suitable for use in the oral environment, including colorants, flavorants, antimicrobials, fragrance, stabilizers, viscosity modifiers and fluoride releasing materials. For example, a fluoride releasing glass may be added to the materials of the invention to provide the benefit of long-term release of fluoride in use, for example in the oral cavity. Fluoroaluminosilicate glasses are particularly preferred. Particularly preferred are silanol treated fluoroaluminosilicate glass fillers, as described in U.S. Pat. No. 5,332,429, the disclosure of which is expressly incorporated by reference herein. Other suitable adjuvants include agents that impart fluorescence and/or opalescence.

In a preferred method of using the dental material of the invention, comprising a hardenable resin and fillers of the invention, the material is placed near or on a tooth surface, followed by a manipulation by the practitioner or laboratory to change the topography of the material, then hardening the resin. These steps can be followed sequentially or in a different order. For example, in a preferred embodiment where the dental material is a mill blank or a prosthesis, the hardening step is generally completed prior to changing the topography of the material. Changing the topography of the material can be accomplished in various ways, including manual manipulation using hand held instruments, or by machine or computer aided apparatus, such as a CAD/CAM milling machine in the case of prostheses and mill blanks. Optionally, a finishing step can be performed to polish, finish, or apply a coating on the dental material.

The following examples are given to illustrate, but not limit, the scope of this invention. Unless otherwise indicated, all parts and percentages are by weight Test Methods Average Particle Diameter Determination Samples approximately 80 nm thick are placed on 200 mesh copper grids with carbon stabilized formvar substrates (SPI Supplies- a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 Kv. A population size of about 50–100 particles can be measured and an average diameter is determined.

Cluster Size Determination

Cluster size distribution was determined by sedimentation techniques using a Sedigraph Model 5100 (Micrometrics, Norcross, Ga.). Specific density of the filler was determined by using an Accupyc 1330 Pycometer (Micrometrics, Norcross, Ga.). A dispersant solution was prepared as follows. To 2880 g of water was added 8.0 g of Tween 80 (Aldrich Chemical Co., Milwaukee, Wis.), 3.2 g sodium hexametaphosphate 66.8–68.0 assay (Matheson Coleman & Bell, Cincinnati, Ohio), 0.08 g sodium fluoride (>99% assay, Aldrich Chemical Co., Milwaukee, Wis.), 8.0 g Liqui-Nox (Alconox, Inc., New York, N.Y.), and 320.0 g eglycerol 99.5% by volume (Aldrich Chemical Co., Milwaukee, Wis.). The pH of the solution was adjusted with the contents of 4 tablets from pHydration Capsules pH7.00 (Micro Essential Laboratory Inc., Brooklyn, N.Y.). An 80 ml portion of the above solution was added to the 5.0 g of filler. The resultant slurry was sonicated for 9 minutes using a W-225 Sonicator Processor (Heat Systems Ultrasonics Inc., Farmingdale, N.Y.) with the output control knob set at 7, and the percent (%) Duty Cycle set at 70%. Cluster size distribution of the filler was determined by the Sedigraph Model 5100.

Crystallinity Index Procedure

Particle size of the phase standard (zirconium oxide, calcium stabilized Z-1083 Lot Number 173077-A-1, CERAC Inc, Milwaukee, Wis.) was reduced by ball milling and/or hand grinding using a boron carbide mortar and pestle to pass 325 mesh sieve. Individual mixtures were prepared consisting of 0.400 grams of sample and 0.100 grams of mass standard, a material incorporated into samples being evaluated for crystallinity index to normalize X-ray intensity values based on amount of material present in a sample. Tungsten metal powder (<3 $\mu$m) was the mass standard used. Mixtures of the samples were blended under ethanol using an agate mortar and pestle and allowed to dry under flowing nitrogen. A similar mixture composed of the phase standard was also prepared to serve as the crystallinity index reference. The dried mixtures were removed from the mortar and pestle by spatula and fine brush and subsequently transferred to individual sample containers. Portions of each sample were prepared as ethanol slurries on sample holders containing flush mounted glass inserts. Multiple X-ray diffraction scans were obtained from each sample and phase standard mixture by use of a vertical Bragg-Bretano diffractometer (constructed by Philips Electronic Instruments, Mahwah, N.J.) employing copper $K_\alpha$ radiation, variable incident slit, fixed exit slit, graphite diffracted beam monochromator, and proportional counter registry of the scattered radiation. Scans were conducted from 25–55 degree (2θ) employing a 0.04 degree step size. A 4 second dwell time was used for standard mixture while a 20 second dwell time was employed for sample mixtures to improve counting statistics. A minimum of 10 scans should be taken. The X-ray generator (Spellman High Voltage Electronics Corporation, Hauppage, N.Y.) was operated at a setting of 40 kV and 20 mA. Peak areas for the observed diffraction maxima due to zirconia and tungsten phases were measured by profile fitting observed diffraction peaks within the 25–55 degree (2θ) scattering angle range. The following peak areas were evaluated depending on the zirconia phase found to be present:

cubic (1 1 1), (2 0 0), and (2 2 0)
tetragonal (1 0 1), (0 0 2)/(1 1 0), and (1 1 2)/(2 0 0)
monoclinic (−1 1 1), (1 1 1), (0 0 2), (0 2 0), and (2 0 0)

The X-ray scattering of internal mass standard was evaluated by measurement of cubic tungsten (1 1 0) peak area. A Pearson VII peak shape model and linear background model were employed in all cases. The profile fitting was accomplished by use of the capabilities of the JADE (version 3.1, Materials Data Inc. Livermore, Calif.) diffraction software suite. The peak areas of zirconia peaks outlined above were summed to produce a total zirconia scattered intensity value [(Zirconia Area)$_{sample}$] for each sample as well as standard [(Zirconia Area)$_{standard}$]. These total zirconia scattered intensity values were divided by respective cubic tungsten (1 1 0) peak areas to produce the ratio [$R_{sample}$] for each sample as well as the phase standard [$R_{standard}$]. The arithmetic mean of $R_{sample}$ and $R_{standard}$ are calculated using individual values obtained from the multiple runs of sample and standard, repectively. The crystallinity index [$X_c$] for each sample was calculated as the ratio of $R_{sample(mean)}$ to $R_{standard(mean)}$.

$R_{sample(i)}$=[(Total Zirconia Area)$_{sample}$]/[(Tungsten Area)$_{sample}$]

$R_{standard(i)}$=[Total Zirconia Area)$_{standard}$]/[(Tungsten Area)$_{standard}$]

$R_{sample(mean)}$=[$\Sigma R_{sample(i)}$]/$N_{sample}$ where $N_{sample}$=number of sample scans $R_{standard(mean)}$=[$\Sigma R_{standard(i)}$]/$N_{standard}$ where $N_{standard}$=number standard scans $X_c$=$R_{sample(mean)}$/$R_{standard(mean)}$ Diametral Tensile Strength (DTS) and Compressive Strength (CS) Testing ADA ("American Dental Association") specification No. 9 and ADA specification No. 27 respectively of ISO-test procedure 4049 (1988) were followed for all DTS and CS testing. Specifically, for determination of compressive strength ("CS") and diametral tensile strength ("DTS"), the composition was packed into a 4 mm inside diameter glass tube, capped with silicone rubber plugs and axially compressed at about 0.28 MPa for 15 minutes, then light cured for 80 seconds by exposure to two oppositely-disposed Visilux units. Each sample was then irradiated for 90 seconds using a Dentacolor XS unit (Kulzer, Inc., Germany). Cured samples were cut on a diamond saw to form cylindrical plugs 8 mm long for measurement of CS and 2 mm long for measurement of DTS. The plugs were stored in distilled water at 37° C. for 24 hours. CS and DTS values for each composition were measured using an Instron™ (Instron 4505, Instron Corp. Canton, Mass.).

The compressive strength (CS) of these samples was tested on an Instron with 10 kN load cell. A total of 5 cylinders of cured composite with about 8 mm length and 4 mm diameter were prepared.

The Diametral Tensile Strength (DTS) of these samples was tested on an Instron with 1 kN load cell. A total of 5 cylinders of cured composite with about 2 mm length and 4 mm diameter were prepared.

Visual Opacity and Radiopacity Testing

Disc-shaped 1 mm thick by 20 mm diameter samples of the composite were cured by exposing them to illumination from an Visilux 2™ (3M Co, St. Paul, Minn.) curing light for 60 seconds on each side of the disk at a distance of 6 mm. The cured composite samples were then evaluated for visual opacity and radiopacity as follows.

Cured composite samples were measured for direct light transmission by measuring transmission of light through the thickness of the disk using a MacBeth transmission densitometer Model TD-903 equipped with a visible light filter, available from MacBeth (MacBeth., Newburgh & N.Y.).

For radiopacity evaluation, the procedure used followed the ISO-test procedure 4049 (1988). Specifically, cured composite samples were exposed to radiation using a Gendex GX-770 dental X-ray (Milwaukee, Wis.) unit for 0.73 seconds at 7 milliamps and 70 kV peak voltage at a distance of about 400? millimeters. The X-ray negative was developed using a Air Techniques Peri-Pro automatic film processor. (Hicksville, N.Y.).

Toothbrush Abrasion Resistance Test

A rectangular 20×9×3 mm thick paste of each example was cured with a Visilux 2™ (3M Co., St. Paul, Minn.) for 60 seconds followed by additional curing for 90 seconds in a Dentacolor™ light box (Kulzer, Inc., Germany).

Preparation of the examples for the Toothbrush Abrasion Resistance Test was based on the guidelines in ASTM-E3-95 "Standard Practice for Preparation of Metallographic Specimens." The specifics for each step, as shown in Table A, were chosen to produce the best final polish for the examples. One face of each each was Au/Pd coated with a Denton Desk II Cold Sputter/Etch Unit (Denton Vacuum, Inc. Moorestown, N.J.) (30 seconds, 2 sputters, 30 mA) to insure adequate adhesion to the epoxy. Each example was placed into cylindrical 31.75 mm by 19.05 mm deep molds. The molds were filled with Buehler's Epoxide™ (Buehler Ltd., Bluff, Ill.) and allowed to cure for 24 hours. The mounted examples were polished according to the following procedure where a series of steps were performed sequentially as shown in Table A, using a Buehler ECOMET 4 Polisher with an AUTOMET 2 Polishing Head. A flat test surface with Ra roughness of less than 25 nm was produced, the largest acceptable starting Ra for the toothbrushing abrasion resistance test as calculated according to the procedures described in "Perthometer, Surface Texture Parameters" (Mahr GMBH, Gottingen, Germany ed. Sep. 1, 1999).

The surface of each of the examples was cleaned with isopropyl alcohol and placed into an ultrasonic cleaner for approximately 60 seconds between each step to avoid contamination.

The lower half of each rectangular polished example was covered with tape to provide a "polished only" surface as the reference, or control, surface. The exposed cured surface was brushed with a ORAL B™ 35 Soft Straight toothbrush (Oral B Laboratories, Belmont, Calif.) under a load of 5N of force at a frequency of 150 cycles/min (2.5 hz). The cured surface and toothbrush were immersed in a slurry of 50/50 by weight CREST™ Regular Flavor (Proctor & Gamble, Cincinnati, Ohio) toothpaste/distilled water during the brushing process. Toothbrushing on each sample was stopped after a 5000 stroke cycle. After toothbrushing, the "polished and brushed" surface was rinsed with water and the tape was removed. The rectangular sample was dried.

The roughness measurements for each "polished only" and "polished and brushed" example were obtained using a WYKO RST PLUS Surface Profiling System (WYKO Corporation, Tuscon, Ariz.). A 50x/0.55 NA objective and 0.5 transfer lens were used to image the samples. The data was collected in accordance with WYKO RST PLUS Operators Manual, using the VSI or Vertical Scanning Interferometry mode with the following instrumental conditions: Modulation threshold 1%, 0.636 microns per pixel, 368×238 pixels, and a standard scan speed.

Roughness, Ra, (DIN and ISO 4287 standard Ra) was calculated according to the procedures described in "Perthometer, Surface Texture Parameters" (Mahr GMBH, Gottingen, Germany ed. Sep. 1, 1999) using the software Vision™ (WYKO Corp., Tucson, Ariz.). The "cylinder" and "tilt" correction were selected in the software. The Ra number was calculated from an "area" or image, which was 174 $\mu$m×234 $\mu$m. An average Ra based on five areas for "polished and brushed" areas, and for "polished only" areas, on each example was collected. Overall average Ra for a "polished only" area of an example was not greater than 25 nm.

TABLE A

Polishing Steps

| Step # | Surface | Abrasive | Lubricant | Force (N/sample) | Platen Rotation | Speed (rpm) | Time |
|---|---|---|---|---|---|---|---|
| 1 | SiC | 120 grit | Water | 22 N/smpl | Complete | 150 | (:20) 2x |
| 2 | SIC | 320 grit | Water | 22 N/smpl | Complete | 150 | (:20) |
| 3 | SiC | 600 grit | Water | 22 N/smpl | Complete | 150 | (:20) 2x |
| 4 | Polimet* | 15 $\mu$m Metadi Diamond Susp* | Metadi Fluid Extender* | 22 N/smpl | Complete | 150 | (1:30) 1:00) |
| 5 | Polimet* | 9 $\mu$m Metadi Diamond Susp* | Metadi Fluid Extender* | 22 N/smpl | Complete | 150 | (2:00) 2x |
| 6 | Textmet* | 3 $\mu$m Metadi Diamond Susp* | Metadi Fluid Extender* | 22 N/smpl | Complete | 150 | (2:00) (1:00) |
| 7 | Microcloth* | Master-polish* | Water | 9 N/smpl | Complete | 150 | (2:00) (1:30) |

*Registered trademark of Buehler, LTD.

| Abbreviations as used in Examples | Description and/or Trade Name | Supplier |
|---|---|---|
| BISEMA6 | ethoxylated (6 mole ethylene oxide) bisphenol A dimethacrylate | Sartomer CD541 (Union Carbide) |
| UDMA | Diurethane dimethacrylate, CAS No. 41 137-60-4, which is commercially available as Rohamere 6661-0 | Rohm Tech, Inc. (Malden, MA) |
| BisGMA | 2,2-bis[4-(2-hydroxy-3-methacryloyloxy propoxy)phenyl]propane | |
| TEGDMA | Triethyleneglycol dimethacrylate | |
| CPQ | Camphorquinone | |
| DPI PF6 | Diphenyl Iodonium Hexafluorophosphate | |
| EDMAB | Ethyl 4-dimethylaminobenzoate | |
| BHT | 2,6-Di-tert-butyl-4-methylphenol | |
| Norbloc 7966 | (CAS 96478-09-0) 2-(2'-Rydroxy-5'-methacryloxyethylphenyl)-H-benzotriazole | Janssen Pharmaceutica |
| Tinuvin-P | 2-(2H-Benzotriazol-2-yl)-4-methylphenol | Ciba-Geigy |
| TFAA | Trifluoroacetic acid | Aldrich (Milwaukee, WI) |
| A174 | γ-methacryloxypropyltrimethoxysilane | Witco Osi Specialties (Danbury, CT) |
| Nalco 1042 | colloidal silica sol containing 33–36% solids, a nitric acid stabilized colloidal silica sol with a pH of about 3.2 | commercially available from Nalco Chemicals |
| Nalco 2329 | colloidal (nano-sized) SiO2 in water containing 40 wt % solids, sodium counter ion, a pH = 8.4, and particle size 75 nm | Nalco Naperville, IL) |
| Zirconia Sol | US. Pat. No. 5,037,579 an aqueous 33% ZrO2 | |
| Silux Plus | Silux Plus ® Anterior Restorative, 3MTM | 3M Co. (St. Paul, MN) |
| 3M ® Z100 | Z100 ® Restorative | 3M Co. (St. Paul, MN) |
| Methoxypropanol | Methoxy-2-propanol | Aldrich (Milwaukee, WI) |
| MEI zirconyl acetate | zirconyl acetate | Magnesium Elektron, Inc. (Flemington, NJ |

EXAMPLES

Preparatory Examples
Resin A

| Constituent | PBW |
|---|---|
| bis-GMA | 24.18% |
| UDMA | 33.85% |
| bis-EMA6 | 33.85% |
| TEGDMA | 4.84% |
| CPQ | 0.2% |
| DPIHFP | 0.5% |
| EDMAB | 1.0% |
| BHT | 0.1% |
| Norbloc 7966 | 1.5% |

Filler Preparation

Preparatory Example A: Preparation of Nanocluster Filler

A 5.0 kg portion of Nalco 1042 sol was weighed out, and the pH of the sol was adjusted to 2.5 using dilute nitric acid. The pH-adjusted sol was added slowly to 2.95 kg of MEI zirconyl acetate and stirred for 1 hour. This mixture was then spray-dried using a 3-foot Niro Spray Drier (Niro 3-foot Mobile Minor™ Spray Drier, Columbia, Md.) at 325° C. inlet temperature and 120° C. outlet temperature. The resulting filler was heat-treated (calcined) at 550° C. for 4 hours to remove the organic portion of zirconyl acetate. The calcined filler was ball-milled for 160 hours to achieve an average cluster size of 1 micron. Crystallinity index of the milled filler was determined to be 0.03.

Preparatory Example B: Treatment of Nanocluster Filler

To a 20 g portion of nanocluster filler as prepared in Preparatory Example A was added 40 g of water followed by thorough mixing with a magnetic stir bar for two minutes to yield a homogenous mixture. The pH of the solution was adjusted to 3–3.3 with trifluoroacetic acid (TFAA). A 2 g amount of A174 was then added to the beaker. The contents were mixed thoroughly using a magnetic stir bar for 120 minutes and then spray-dried using a Buchi spray drier (Buchi/Brinkmann Mini Spray Dryer Model 190, Brinkmann Instruments, Inc. Westbury, N.Y.) at 200° C. inlet temperature and 85° C. outlet temperature.

Preparatory Example C: PAMA Synthesis (2-hydroxymethyl-2-[(N-methacryloxyethyl) carbamoylmethyl]propionic acid)

The reactor was first charged with an excess amount of 2,2-bis(hydroxymethyl)propionic acid (BHMPA) (139.94 g, 1.043 mole), 2,6-Di-tert-butyl-4-methylphenol (0.2322 g, 1.054 mmole), triphenyl antimony (0.1891 g, 0.536 mmole), and dibutyltin dilaurate (0.6801 g, 1.077 mmole). The starting material, BHMPA, was only slightly soluble in THF at room temperature. Isocyanatoethylmethacrylate (IEM) was gradually dripped (80.94 g, 0.522 mole) into the above mixture. The reaction was run at 60° C. for 24 hours while stirring constantly. At the end of the reaction, most of the unreacted BHMPA settled out as white solid powder after the solution was cooled down. Unreacted BHMPA was filtered off by vacuum filtration, and the solvent was then stripped off. The recovered BHMPA could be used in future reactions.

After the removal of the solvent, the product became slightly cloudy due to slow precipitation of residual BHMPA. Enough diethyl ether was added to dissolve the product and then the solution was allowed to sit overnight (approximately 18 hours) undisturbed to precipitate out most of the remaining BHMPA in solution. The white precipitate was filtered off by vacuum filtration, and diethyl ether was stripped off.

The resulting product, 2-hydroxymethyl-2-[(N-methacryloxyethyl)carbamoylmethyl]propionic acid (PAMA) was a colorless, flowable liquid. The purity of PAMA in the final product was approximately 80% by molar ratio, with 2,2-di(N-methacryloxyethyl carbamoylmethyl) propionic acid (PDMA) being the main side-product (approximately 17%) and small amounts of remaining BHMPA (approximately 3%).

Example 1

A composite material was prepared by thoroughly mixing 22 pbw resin A and 78 pbw nanocluster filler of preparatory example B. The material was cured and the mechanical and optical properties evaluated according to the Radiopacity, Visual Opacity (VO), Compressive Strength (CS) and Diametral Tensile Strength (DTS) methods previously described. The physical properties were compared with a standard anterior restorative material, Silux ™Plus Anterior Dental Restorative (3M CO, St. Paul, Minn.) (Silux Plus), in Table 1.

TABLE 1

| Example | DTS (MPa) | CS (MPa) | Visual opacity | Radiopacity |
| --- | --- | --- | --- | --- |
| Example 1 | 68.90 | 378.90 | 0.18 | 1.8 |
| Silux Plus | 49.52 | 358.12 | 0.35 | 0.26 |

Example 1 produced radiopacity of 1.8, which is sufficiently radiopaque.

Examples 2–5

For each material of examples 2–5, a 20 g portion of nanocluster filler as prepared in preparatory example B was added to 40 g of water followed by thorough mixing for two minutes. The pH of the solution was adjusted to 3–3.3 with TFAA. Different amounts of silane A174 as listed in Table 3 were added to the beaker to make each material. The contents were mixed thoroughly using a magnetic stir bar for 120 minutes and then spray-dried using a Buchi spray drier at 200° C. inlet temperature and 85–100° C. outlet temperature. The four materials were prepared to contain 78% of the various fillers and 22% of resin A. The materials were cured and the mechanical properties of the cured dental composites evaluated according to the Compressive Strength (CS) and Diametral Tensile Strength (DTS) methods previously described.

TABLE 3

| Example | Wt % of silane A174/g filler | DTS (MPa) | CS (MPa) |
| --- | --- | --- | --- |
| Example 2 | 5 | 47.24 | 346.74 |
| Example 3 | 10 | 68.90 | 378.90 |
| Example 4 | 15 | 71.03 | 357.94 |
| Example 5 | 20 | 57.79 | 372.57 |

A silane loading of 10–15 wt. % of silane A174/g filler produced optimal strength.

Examples 6–7

The possibility of using nanocluster and nanofiller together was tested. For the nanocluster filler component, filler of Preparatory Example B was made. For the nanosilica component, filler particles were made by thoroughly mixing 250 g Nalco 2329, 281.0 g methoxy-2-propanol and 3.72 g of A174. The Nalco 2329 was weighed into a 2 L beaker. The alcohol and silane were weighed into a 1 L beaker and mixed together. The alcohol solution was added to the silica sol slowly with swirling (1–2 min). The resultant mixture was reacted at 80° C. for 16 hr to produce a modified silica sol. A 1 kg portion of water was added to the modified silica sol. This mixture was spray-dried using a Buchi spray drier at 200° C. inlet temperature and 85–1000° C. outlet temperature. For the nanozirconia component, filler was prepared by mixing together 14.95 g MEEAA and 210 g of Zirconia Sol of U.S. Pat. No. 5,037,579. Thorough mixing for two minutes yielded a homogenous mixture. A solution of 24.36 g of Preparatory Example C in 25 g of ethanol was then added to the beaker. The contents were mixed thoroughly using a magnetic stir bar for 60 minutes followed by spray-drying using a Buchi spray drier at 200° C. inlet temperature and 85–100° C. outlet temperature.

Two materials for examples 10–11 containing a total of 78% pbw fillers, as shown in Table 5, and 22% pbw resin A were made. The materials for examples 10–11 and Silux Plus were cured, and the mechanical properties of the three dental composites were evaluated according to the Compressive Strength (CS), Visual Opacity (VO) and Diametral Tensile Strength (DTS) methods previously described and compared to Silux Plus.

TABLE 4

| Example | Nano-cluster | Nano-silica Particle | Nano-Zirconia | CS (Mpa) | DTS (Mpa) | VO |
| --- | --- | --- | --- | --- | --- | --- |
| Example 6 | 31.2 | 31.2 | 15.6 | 411.88 | 56.90 | 0.40 |
| Example 7 | 39.0 | 39.0 | 0.0 | 381.63 | 71.03 | 0.49 |
| Comparative Silux Plus | NA | NA | NA | 358.12 | 49.52 | 0.35 |

NA = Not applicable

Example 8

Example 8 was made using the method described for making example 1. In Table 5, surface roughness, Ra, before and after toothbrushing was calculated as described in the Toothbrush Abrasion Resistance Test for example 8 Silux Plus and Z100.

TABLE 5

| Example | Surface Roughness after polishing before toothbrushing (Ra$_{Average for polished area of example}$) Average of 5 area readings (μm) | Surface Roughness after tooth brushing (Ra$_{Average for polished and brushed area of example}$) Average of 5 area readings (μm) |
| --- | --- | --- |
| Comparative Z100 | 0.015 | 0.268 |
| Comparative Silux Plus | 0.019 | 0.089 |
| Example 8 | 0.019 | 0.130 |

Example 9

Scotchbond™ adhesive 62 wt % (3M Co., St. Paul, Minn.) was thoroughly mixed with 38 wt % Filler of Preparatory Example B to make Example 9. Adhesive strength to enamel and dentin are reported in Table 6.

Adhesive strength to dentin and enamel of the adhesive was evaluated by the following procedure. Five bovine teeth of similar age and appearance were partially embedded in circular acrylic discs. The exposed portion of each tooth was ground flat and parallel to the acrylic disc using Grade 120 silicon carbide paper-backed abrasive mounted on a lapidary wheel, in order to expose the dentin or enamel. During this and subsequent grinding and polishing steps, the teeth were continuously rinsed with water. Further grinding and polishing of the teeth was carried out by mounting Grade 600 silicon carbide paper-backed abrasive on the lapidary wheel.

The polished teeth were stored in distilled water, and used for testing within 2 hours after polishing. The polished teeth were removed from the water and blotted dry. Using a Scotchbond™ kit 7540S (3M Co., St. Paul, Minn.), Scotchbond™ etchant was painted onto each of the polished tooth surfaces with a brush, allowed to stand for 15 seconds, rinsed with distilled water and then blotted dry. A single drop of Scotchbond™ primer was painted onto each of the polished tooth surfaces with a brush and immediately blown dry with compressed air for 5 sec.

Adhesive of example 9 was painted onto each of the tooth surfaces, and hardened using a 10-second irradiation with a Visilux 2™ dental curing light. Previously prepared molds made from a 2-mm thick TEFLON™ (E.I. DuPont de Nemours, Wilmington, Del.] sheet with a 4 mm diameter hole through the sheet were clamped to each prepared tooth so that the central axis of the hole in the mold was normal to the tooth surface. The hole in each mold was filled Z100 and hardened with a Visilux 2™ dental curing light using a 40-second irradiation.

The teeth and molds were stored in distilled water at 37° C. for approximately 24 hours. The molds were then carefully removed from the teeth, leaving a molded button of restorative attached to each tooth.

Adhesive strength was evaluated by mounting the acrylic disk in a holder clamped in the jaws of an Instron apparatus with the polished tooth surface oriented parallel to the direction of pull. A loop of orthodontic wire (0.44 mm diameter) was placed around the restorative button adjacent to the polished tooth surface. The ends of the orthodontic wire were clamped in the pulling jaw of the Instron apparatus, thereby placing the bond in shear stress. The bond was stressed until it (or the dentin or button) failed, using a crosshead speed of 2 mm/min.

TABLE 6

| | Enamel | | Dentin | |
| --- | --- | --- | --- | --- |
| Example | Adhesion Strength (Mpa) | STDev (MPa) | Adhesion Strength (MPa) | STDev (MPa) |
| 9 | 22.5 | 4.9 | 23.0 | 1.5 |

Good adhesion was observed.

What is claimed is:

1. A filler for dental materials comprising a substantially amorphous cluster comprising:
   non-heavy metal oxide particles, and
   amorphous heavy metal oxide particles having an average diameter of less than about 100 nm.

2. The filler of claim 1 wherein said cluster has an average diameter of less than about 5 μm.

3. The filler of claim 1 wherein said non-heavy metal oxide particles have an average diameter of less than about 100 nm.

4. The filler of claim 1 wherein said heavy metal oxide particles are aggregated particles having an average diameter of less than about 100 nm.

5. The filler of claim 1 wherein said cluster has a crystallinity index of about 0.1.

6. The filler of claim 1 wherein said heavy metal oxide is selected from a heavy metal having an atomic number greater than 30.

7. The filler of claim 1 wherein said heavy metal oxide is selected from the group consisting of zirconium oxide, cerium oxide, tin oxide, yttrium oxide, strontium oxide, barium oxide, lanthanum oxide, zinc oxide, ytterbium oxide, bismuth oxide and mixtures thereof.

8. A filler for dental materials comprising a substantially amorphous cluster comprising:
   silica particles, and
   amorphous heavy metal oxide particles having an average diameter of less than about 100 nm.

9. The filler of claim 8 wherein said cluster has an average diameter of less than about 5 μm.

10. The filler of claim 8 wherein said cluster has an average diameter of less than about 2 μm.

11. The filler of claim 8 wherein said cluster has a crystallinity index of about 0.1.

12. The filler of claim 8 wherein said cluster has a crystallinity index of about 0.05.

13. The filler of claim 8 wherein said silica particles have an average diameter of less than about 100 nm.

14. The filler of claim 8 wherein said silica particles have an average diameter of less than about 50 nm.

15. The filler of claim 8 wherein said silica particles have an average diameter of less than about 40 nm.

16. The filler of claim 8 wherein said heavy metal oxide is selected from a heavy metal having an atomic number greater than 30.

17. The filler of claim 8 wherein said heavy metal oxide is selected from the group consisting of zirconium oxide, cerium oxide, tin oxide, yttrium oxide, strontium oxide, barium oxide, lanthanum oxide, zinc oxide, ytterbium oxide, bismuth oxide and mixtures thereof.

18. The filler of claim 8 wherein said heavy metal oxide particles are aggregated particles having an average diameter of less than about 100 nm.

19. The filler of claim 8 wherein said heavy metal oxide particles have an average diameter of less than about 50 nm.

20. The filler of claim 8 wherein said heavy metal oxide particles have an average diameter of less than about 10 nm.

21. A dental material comprising the filler of claim 1 and a hardenable resin.

22. The dental material of claim 21 wherein said hardenable resin is selected from the group consisting of acrylates, methacrylates, epoxies, and mixtures thereof.

23. The dental material of claim 21 wherein the material is selected from the group consisting of dental restoratives, dental adhesives, casting materials, dental cements, dental sealants, and dental coatings.

24. The dental material of claim 21 wherein the material, after hardening and subjecting to the Toothbrush Abrasion Resistance Test, has a surface roughness of less than about 0.2 μm.

25. The dental material of claim 21 wherein the material, after hardening, has a compressive strength greater than about 35 MPa.

26. The dental material of claim 21 wherein the material, after hardening, has a diametral tensile strength of greater than about 15 MPa.

27. The dental material of claim 21 wherein the material, after hardening, has a visual opacity of about 0.05 to 0.5.

28. A dental material comprising the filler of claim 8 and a hardenable resin.

29. The dental material of claim 28 wherein said hardenable resin is selected from the group consisting of acrylates, methacrylates, epoxies, and mixtures thereof.

30. The dental material of claim 28 wherein the material is selected from the group consisting of dental restoratives, dental adhesives, dental casting materials, dental cements, dental sealants, and dental coatings.

31. The dental material of claim 28 further comprising a polymerization initiator system for hardening said resin.

32. The dental material of claim 28 wherein the material, after hardening and subjecting to the Toothbrush Abrasion Resistance Test, has a surface roughness of less than about 0.2 μm.

33. The dental material of claim 28 wherein the material, after hardening and subjected to the Toothbrush Abrasion Resistance Test, has a surface roughness of less than about 0.15 μm.

34. The dental material of claim 28 wherein the material, after hardening, has a compressive strength greater than about 35 MPa.

35. The dental material of claim 28 wherein the material, after hardening, has a compressive strength greater than about 200 MPa.

36. The dental material of claim 28 wherein the material, after hardening, has a compressive strength greater than about 350 MPa.

37. The dental material of claim 28 wherein the material, after hardening, has a diametral tensile strength of greater than about 15 MPa.

38. The dental material of claim 28 wherein the material, after hardening, has a diametral tensile strength of greater than about 40 MPa.

39. The dental material of claim 28 wherein the material, after hardening, has a diametral tensile strength of greater than about 60 MPa.

40. The dental material of claim 28 wherein the material, after hardening, has a visual opacity of about 0.05 to to 0.5.

41. The dental material of claim 28 wherein the material, after hardening, has a visual opacity of about 0.05 to about 0.35.

42. The dental material of claim 28 wherein the material, after hardening, has a visual opacity of about 0.05 to about 0.25.

43. A method of making a filler for dental material comprising:
    admixing a non-heavy metal oxide sol with a heavy metal oxide sol;
    drying said mixed sol into a dried product;
    calcining said dried product; and
    milling said calcined product;
wherein said filler is a substantially amorphous cluster comprising non-heavy metal oxide particles and a heavy metal oxide.

44. The method according to claim 43 further comprising surface modifying said milled product.

45. A method of making a dental material comprising:
    admixing a non-heavy metal oxide sol with a heavy metal oxide sol;
    drying said mixed sol into a dried product;
    calcining said dried product;
    milling said calcined product; and
    admixing said milled product with a hardenable resin.

46. A method of using the dental material of claim 21 comprising:
    placing said material near or on a tooth surface;
    changing the topography of said material; and
    hardening said material.

47. The method according to claim 46 wherein placing, changing, and hardening are performed sequentially.

48. The method according to claim 46 further comprising finishing the surface of said hardened material.

49. A method of using the dental material of claim 28 comprising:
    placing said material near or on a tooth surface;
    changing the topography of said material; and
    hardening said material.

50. The method according to claim 49 wherein placing, changing, and hardening are performed sequentially.

51. The method according to claim 49 further comprising finishing the surface of said hardened material.

52. A filler for dental materials comprising a substantially amorphous cluster comprising:
    non-heavy metal oxide particles having an average diameter of less than about 100 nm, and
    amorphous metal oxide particles having an average diameter of less than about 100 nm,
wherein the metal has an atomic number greater than 28, and wherein the cluster has an average diameter of less than about 5 μm.

53. A filler for dental materials comprising a substantially amorphous cluster comprising:
    silica particles having an average diameter of less than about 100 nm, and
    amorphous metal oxide particles having an average diameter of less than about 100 nm,
wherein the metal has an atomic number greater than 28, and wherein the cluster has an average diameter of less than about 5 μm.

54. A dental article preparable by a method comprising hardening the dental material of claim 21 to fabricate a dental article selected from the group consisting of dental mill blanks, dental prostheses, orthodontic devices, artificial crowns, anterior fillings, posterior fillings, and cavity liners.

55. A method of using the dental material of claim 28 comprising hardening the material to fabricate a dental article selected from the group consisting of dental mill blanks, dental prostheses, orthodontic devices, artificial crowns, anterior fillings, posterior fillings, and cavity liners.

* * * * *

UNITED STATES PATENT AND TRADEMARK OFFICE
CERTIFICATE OF CORRECTION

PATENT NO.    : 6,730,156 B1
DATED         : May 4, 2004
INVENTOR(S)   : Windisch, Mark S.

It is certified that error appears in the above-identified patent and that said Letters Patent is hereby corrected as shown below:

<u>Title page,</u>
Item [56], References Cited, OTHER PUBLICATIONS, "Synthesis and Collodial, reference, delete "Collodial" and insert -- Colloidal --, therefore; delete "Y203" and insert -- $Y_2O_3$ --, and delete "ZrO2" and insert -- $ZrO_2$ --, therefore;
"The Role of Complexing Ligants in the Formation of Non-Aggregatated Nanoparticles of Zirconia," reference, delete "Ligants" and insert -- Ligands --, therefore;
"Determination of Polymerization Shrinkage Kinetics" reference, delete "of" and insert -- in --, therefore; insert -- " -- before "Technical",
"Degussa AG Product Brochure," reference, after "Pigments" insert -- " --;
"54468USA1A–09/168,051," reference, delete "Polymerizating" and insert -- Polymerizing --, therefor;

<u>Column 3,</u>
Lines 54-55, delete "Theological" and insert -- rheological --, therefore;

<u>Column 5,</u>
Line 60, delete "Dupont" and insert -- DuPont --, therefore;

<u>Column 8,</u>
Line 51, delete "an" and insert -- can --, therefore;

<u>Column 10,</u>
Line 14, delete "furil" and insert -- furyl --, therefore;

<u>Column 14,</u>
Line 25, insert -- - -- before "phenyl";
Line 44, delete "ie." and insert -- i.e. --, therefore;

<u>Column 15,</u>
Line 62, delete "thienyliodoniun" and insert -- thienyliodonium --, therefore;

<u>Column 16,</u>
Line 33, delete "iodonum" and insert -- iodonium --, therefore;

<u>Column 18,</u>
Line 44, delete "Radeure" and insert -- Radcure --, therefore;

<u>Column 20,</u>
Line 8, delete "Accuracy" and insert -- Accupyc --, therefore;
Line 57, after "weight" insert -- . --;

UNITED STATES PATENT AND TRADEMARK OFFICE
CERTIFICATE OF CORRECTION

PATENT NO. : 6,730,156 B1
DATED : May 4, 2004
INVENTOR(S) : Windisch, Mark S.

It is certified that error appears in the above-identified patent and that said Letters Patent is hereby corrected as shown below:

Column 21,
Line 12, delete "eglycerol" and insert -- glycerol --, therefore;
Line 46, delete "$K_a$" and insert -- $K_\alpha$ --, therefore;

Column 22,
Line 13, delete "repectively" and insert -- respectively --, therefore;
Line 58, delete "1 kN" and insert -- 10kN --, therefore;

Column 23,
Line 18, insert -- XS -- before "light";
Line 24, delete "each" and insert -- example --, therefore;
Line 30, insert -- Lake -- before "Bluff";

Column 24,
Line 32, delete "Tucson" and insert -- Tuson --, therefore;

Columns 25-26, Col. 2 in Table,
Line 3, delete "41 137- 60-4" and insert -- 41137-60-4 --, therefore;
Line 20, delete "SiO2" and insert -- SiO2 --, therefore;

Columns 25-26, Col. 3 in Table,
Line 20, insert -- ( -- before "Naperville";

Columns 25-26, Col. 2 in Table,
Line 23, delete "ZrO2" and insert -- $ZrO_2$ --, therefore;
Line 24, delete "Silux Plus®" and insert -- Silux Plus$^{TM}$ --, and delete "3MTM" and insert -- 3M$^{TM}$ -- therefore;

Columns 25-26, Col. 1 in Table,
Line 25, delete "3M®" and insert -- 3M$^{TM}$ --, therefore;

Columns 25-26, Col. 2, in Table,
Line 25, delete "Z100®" and insert -- Z100$^{TM}$ --, therefore;

Column 25-26, Col. 2, in Table,
Line 28, after "NJ" insert -- ) --;

Column 28,
Line 8, delete "85-1000°" and insert -- 85-100° --, therefore;

UNITED STATES PATENT AND TRADEMARK OFFICE
CERTIFICATE OF CORRECTION

PATENT NO. : 6,730,156 B1
DATED : May 4, 2004
INVENTOR(S) : Windisch, Mark S.

It is certified that error appears in the above-identified patent and that said Letters Patent is hereby corrected as shown below:

Column 31,
Line 34, delete "to" before "0.5".

Signed and Sealed this

Third Day of May, 2005

JON W. DUDAS
*Director of the United States Patent and Trademark Office*